United States Patent [19]

Kaspari

[11] 4,295,471
[45] Oct. 20, 1981

[54] NON-INVASIVE VASCULAR WAVEFORM TRANSDUCER AND APPARATUS

[76] Inventor: William J. Kaspari, 342 Willowbrood Dr., Portola Valley, Calif. 94025

[21] Appl. No.: 42,415

[22] Filed: May 25, 1979

[51] Int. Cl.³ .............................................. A61B 5/02
[52] U.S. Cl. .................... 128/675; 128/687; 128/715; 179/1 ST; 73/774
[58] Field of Search .............. 128/670, 675, 687, 715; 179/1 ST, 139; 73/774, 777

[56] References Cited

U.S. PATENT DOCUMENTS

| | | | |
|---|---|---|---|
| 3,182,129 | 5/1965 | Clark et al. | 128/715 |
| 3,189,023 | 6/1965 | Salz et al. | 128/675 |
| 3,233,041 | 2/1966 | Croslin | 128/715 X |
| 3,387,149 | 6/1968 | Young | 128/715 X |
| 3,555,187 | 12/1966 | Rowley | 179/1 ST |
| 3,573,394 | 4/1971 | Birnbaum | 128/715 |
| 3,682,161 | 8/1972 | Alibert | 128/687 |
| 3,846,585 | 11/1974 | Slosberg et al. | 179/1 ST |

FOREIGN PATENT DOCUMENTS

1483811  5/1967  France ................... 128/715

*Primary Examiner*—Kyle L. Howell
*Attorney, Agent, or Firm*—Lyon & Lyon

[57] ABSTRACT

Apparatus is disclosed herein for non-invasively monitoring arterial waveforms, such as the waveform produced by blood flow through the brachial artery in a human subject. The invention includes a unique transducer which senses both a pressure wave proportional to blood flow in the artery and an acoustical signal proportional to the turbulence created by blood flow through a partially occluded artery. The transducer may be cuff mounted for attachment to the subject, and the cuff may be automatically inflated in accordance with the invention.

11 Claims, 15 Drawing Figures

NON-INVASIVE VASCULAR WAVEFORM TRANSDUCER AND APPARATUS

FIELD OF THE INVENTION

This invention relates generally to blood pressure monitoring devices, and more particularly to non-invasive blood pressure monitoring devices and systems.

BACKGROUND OF THE INVENTION

Blood pressure and heart rate have long been recognized as indicators of the general physical well-being of a patient. Both blood pressure and heart rate are monitored in nearly all medical procedures, from a general physical examination to extensive surgery. Depending upon the condition of the subject and the need for accuracy, various approaches are used, particularly for measuring blood pressure.

For example, the most common method of measuring blood pressure in human subjects is with a stethoscope and sphygmomanometer, in which a nurse or other member of the medical staff inflates the cuff until the brachial artery is occluded and then, while deflating the cuff, listens with the stethoscope for the first Korotkoff sounds in the artery. When the first Korotkoff sounds are heard, the manometer reading is taken as an indication of systolic pressure. Diastolic pressure is indicated by further deflation of the cuff until the Korotkoff sounds indicate, to the nurse, that the vessel is no longer occluded, with the manometer providing the pressure indication.

As those skilled in the art will appreciate, the accuracy of the stethoscope and sphygmamonometer method depends upon the skill of the technician, and also depends on the technician's hearing. The result is that this approach is unreliable for situations requiring high repeatability and accuracy, although the sphymomanometer approach does provide a general indication of blood pressure, and has the advantage of being non-invasive.

The pitfalls of the stethoscope and sphygmomanometer technique are well recognized by the medical profession, and this approach is not used in many surgical contexts where accuracy is important, as in coronary care. In these demanding applications, the more common method of monitoring blood pressure is the intra-arterial catheter. An intra-arterial catheter, while providing improved accuracy, has the obvious drawback of requiring surgical implantation; i.e.—an invasive approach. Thus there has not been, prior to the present invention, a suitable non-invasive technique for monitoring blood pressure and related characteristics which provides satisfactory accuracy and repeatability to be useful in demanding surgical contexts.

In addition, none of the non-invasive devices which has existed previously could, automatically, interpret the signals provided by a transducer to provide indications of heart rate, diastolic and systolic pressures, and other characteristics to a high degree of repeatability.

SUMMARY OF THE INVENTION

The present invention resolves or improves upon many of the limitations of the prior art by providing, non-invasively, indications of heart rate, diastolic and systolic blood pressure and other characteristics of the cardiovascular system which are accurate to a high degree of repeatability.

The present invention includes a novel transducer for detecting the arterial waveform of a subject, located in an inflatable cuff worn by the subject, together with a control device for automatically inflating and deflating the cuff as well as accumulating and analyzing the data provided by the transducer. The control device incorporates novel data accumulation and data analysis techniques. However, the transducer may be used independently of the other portions of the invention. Similarly, the control device and the data accumulation and data analysis methods may be used independently of the remainder of the invention.

The transducer of the present invention is, in one embodiment thereof, mounted in an inflatable cuff for attachment to the body of the subject. In one embodiment, the transducer includes a housing which forms two cavities, one on either side of a central portion. A piezoelectric sensing element is mounted in each cavity, and each sensor is supported in a relatively rigid manner near its outside circumference. With the transducer mounted in the cuff, one of the piezoelectric elements is positioned to sense pressure waves indicative of the arterial waveform directly through the arm. The remaining element, which faces away from the arm, receives pressure waves indicative of the arterial waveform but transmitted via the cuff. A large orifice in the transducer permits good transmission of the arterial pressure waves to the sensing elements, thereby simplifying positioning of the transducer on the subject. The sensing elements then convert the pressure waves into electrical signals. The two sensing elements may be operated in a differential arrangement to provide good common mode rejection, thereby providing a good representation of the arterial waveform.

The signals generated by the transducer are then provided to the control device for data accumulation and analysis. In one embodiment, the analog signals provided by the transducer are converted to a digital format, and the digital signals are periodically sampled during deflation of the cuff to provide a representation of each pulse in excess of a predetermined threshold. The samples are stored in a data memory, and after the cuff is sufficiently deflated the stored data is analyzed to provide systolic and diastolic blood pressures, heart rate, and other indications of cardiovascular condition.

Various techniques are utilized during analysis of the data to ensure the validity thereof, including subjecting the stored data to timing criteria and establishing reference values to aid in the elimination of artifacts. Also, deflation of the cuff may be temporarily inhibited to verify the occurrence of the systolic pulse by ensuring recurrence of the subject's heartbeat at that cuff pressure. Diastolic pressure is determined by an iterative technique which establishes a reference amplitude and repetitively scans the stored data to locate pulses which are within an increasingly narrow range but still indicative of decreasing occlusion of the artery to accurately indicate the pressure at which the artery is no longer occluded by the cuff.

Continuous monitoring of the subject's cardiovascular system may be accomplished by inflating the cuff to a pressure which is less than that necessary to begin occlusion of the blood vessel being monitored, but sufficient to maintain good contact between the subject and the transducer. Since either arteries or veins may be monitored, the pressure in the cuff will be either sub-diastolic or sub-venous. The resultant vascular waveform can then be displayed as a representation of cardiovascular function, or may be calibrated based on the characteristics determined as described above, or may be otherwise analyzed.

It is therefore one purpose of this invention to provide an improved apparatus for indicating the general cardiovascular condition of a subject.

It is a further object of the present invention to provide a device for providing an indication of blood pressure to a high degree of repeatability.

It is still another object of the present invention to provide an apparatus for providing an accurate indication of heart rate, systolic and diastolic blood pressure, and other characteristics.

Other and further objects of the present invention will be better understood from the detailed description which follows, when taken in combination with the appended drawings in which:

FIG. 2b illustrates, in exploded view, the transducer of FIG. 2a.

FIG. 2c illustrates, in cross-sectional side view, the transducer of FIG. 2a.

DETAILED DESCRIPTION OF THE INVENTION

Figure 1:
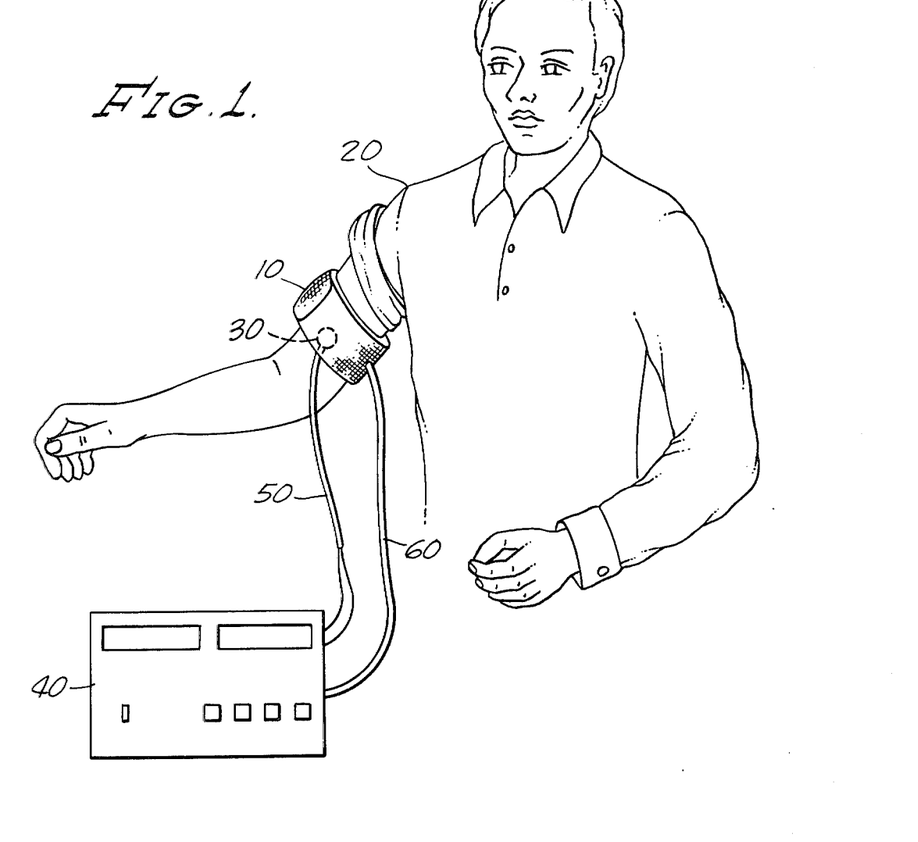
FIG. 1 illustrates the system of the present invention.

Referring first to FIG. 1, there is shown therein a general illustration of the system of the present invention. An inflatable cuff 10 is affixed to the arm of the subject 20 in a conventional manner. The cuff 10 includes a transducer 30, to be described in greater detail hereinafter.

The transducer 30 communicates with a control apparatus 40 through a pair of wires 50 or other similar arrangement. The cuff is susceptible of inflation through an air tube 60, which may also be controlled by the control apparatus 40. The control apparatus 40, which will be described in greater detail in connection with FIGS. 3 and 4, performs data accumulation and analysis functions, and also controls the pneumatics of the present invention.

The operation of the system shown in FIG. 1, although described in detail hereinafter, may be briefly described as follows. Once the cuff 10 is affixed to the subject 20 in a conventional manner, with the transducer 30 located at, preferably, the distal end of the cuff and positioned near the blood vessel to be monitored (such as the brachial artery), control apparatus 40 is activated and causes the cuff to inflate until the artery is fully occluded or, as a safety feature, until a maximum cuff pressure is reached. Full occlusion may be indicated by inflating the cuff for a predetermined period after cessation of Korotkoff sounds or other pressure signals, or by inflating the cuff to a predetermined pressure in excess of the pressure at which signals ceased being detected. Inflation may be caused to occur at a single rate, or may occur at a rapid initial rate followed by a slower rate until occlusion occurs, as described in connection with FIG. 4.

The general procedure for inflation of the cuff is described in U.S. Pat. No. 4,058,117, although novel features of the present invention are more fully described in connection with FIG. 4.

Once the inflation of the cuff is ceased, the control apparatus 40 causes a bleed valve to open automatically, thereby slowly deflating the cuff. As the cuff deflates, Korotkoff sounds begin to be detected by the transducer 30, and the detected data is communicated to the control apparatus 40. The control apparatus 40 validates the data, and stores it for subsequent analysis. The pressure waves generated by blood flow in the vessel and detected by the transducer are stored until either cuff pressure falls too low, or until no valid pulses have been detected for a predetermined time period. The stored data is thereafter analyzed, and various cardiovascular characteristics resulting from such analysis can be displayed by the control apparatus 40.

Figure 2A:
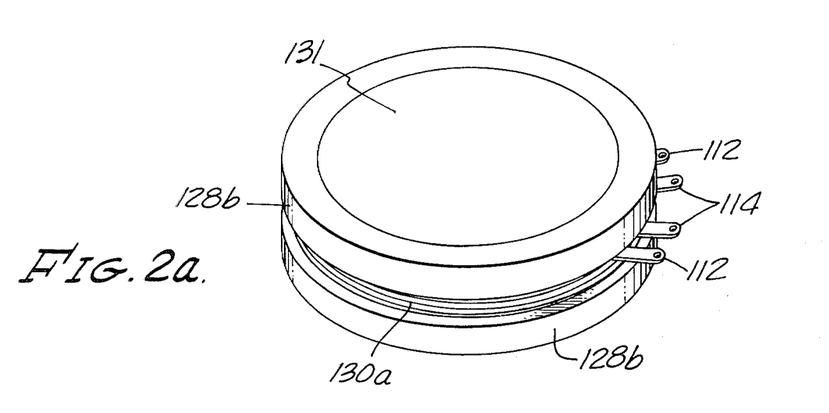
FIG. 2a illustrates one embodiment of the transducer shown in the system of FIG. 1.
Figures 2B, 2C:
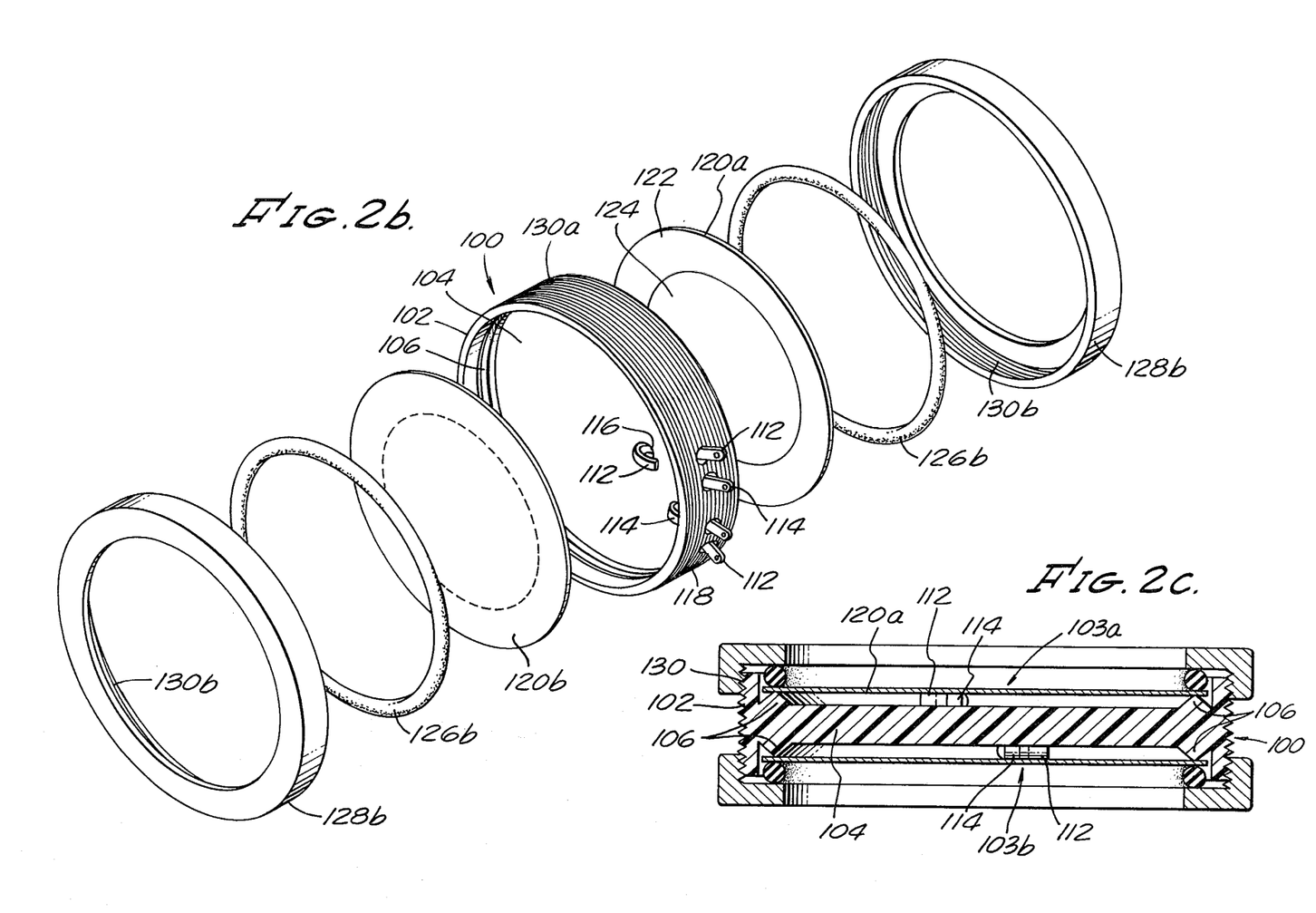

The transducer 30 is comprised of a housing 100, which includes an outer cylindrical portion 102 integral with a center plate 104. The center plate 104 is located substantially at the middle of the cylindrical portion 102, thereby forming two symmetrical cavities 103a and 103b in the housing 100, one on either side of the plate 104.

On each side of the center plate 104 is located a ridge 106 near the cylindrical portion 102. Although the ridge 106 is shown in FIGS. 2b and 2c spaced slightly interior to the internal diameter of the cylindrical portion 102, the ridge 106 may also be contiguous to the cylindrical portion 102. Resting on and supported by each of the ridges 106 are a pair of piezoelectric sensing elements 120a and 120b, one in each cavity 103a and 103b, respectively. Each piezoelectric sensing element 120a-b includes a substrate 122 on which is deposited a pressure sensitive portion 124 approximately in the center thereof. The piezoelectric sensing elements 120a-b may be a Model 101 piezoelectric sensor element manufactured by Gulton Industries, or other suitable device.

The sensing elements 120a-b are positioned in the cavities 103a-b such that pressure sensitive portions 124 thereof touch a contact 112 with a second contact 114 touching the substrate 122 of the sensing elements. The contacts 112 and 114 are located in passages 116 and 118 in the housing 100, and extend through the outer cylindrical wall 102 as shown in FIG. 2b. The two pairs of electrical contacts 112 and 114 thus transmit the electrical signals produced by deformation of the sensing elements 120a-b to the control apparatus 40. If the housing 100 is made of plastic or other electrically non-conductive material, the contacts 112 and 114 need not be insulated. However, if the housing 100 is made from aluminum or other conductive material, the contacts 112 and 114 should be suitably insulated.

Located atop either sensing element 120a-b are O-rings 126a-b, of substantially the same diameter as the ridge 106. The O-rings 126a-b and sensing elements 120a-b are retained in the cavities 103a-b by means of retaining caps 128a-b, which are affixed to the housing 100 by means of threads 130a-b thereon or by other suitable means as described hereinafter. The pressure of the caps 128a-b causes the O-rings 126a-b to exert a force on the sensing elements 120a-b at the ridges 106, thereby clamping the sensing elements 120a-b therebetween while still allowing good flexibility and responsiveness at the center of the sensing elements.

The caps 128a–b, which may be made of either plastic or metal, each have an orifice 130 therethrough, which orifice is preferably made as large as possible to permit the transducer to be easily positioned on the subject to receive the pressure waves generated by dilation and contraction of the artery. Thus the orifice 130 is preferably as large as permitted while still retaining the O-rings 126a–b. To permit good transmission of the arterial waveform to the sensing elements 120a–b once the transducer 30 is assembled as shown in FIG. 2a, that portion of the cavities 103a–b accessible through the orifices 130 is filled flush with a relatively low viscosity silicone rubber 131 such as Dow Corning Sylgard 170 or other suitable material. The arterial waveform which impinges upon the transducer 30 is thus transmitted through the rubber 131 to the sensing elements 120a–b, which convert the pressure waves to electrical signals. The electrical signals are then conveyed to the control apparatus 40 by means of the contacts 112 and 114 and the wires 50.

It can thus be appreciated that the transducer 30 includes two sensing elements 120, each of which independently supplies signals to the apparatus 40. It can likewise be appreciated that only one of the transducer sensing elements is located to receive signals transmitted directly through the arm, and the remaining sensing element will thus be near the cuff 10. As a result, the sensing element which is contiguous to the brachial artery will receive the pressure waveform of the brachial artery directly. Surprisingly, however, the sensing element which is contiguous to the cuff 10 also receives a substantial portion of the arterial waveform. This apparently occurs by transmission of the waveform through the cuff itself to the outward facing sensing element. The substantial advantages of the dual sensing element embodiment of the transducer 30 shown in FIGS. 2a–c will be better appreciated from FIGS. 6a–6e, which shows the improved information that may be obtained with the transducer of the present invention.

Figure 6A:
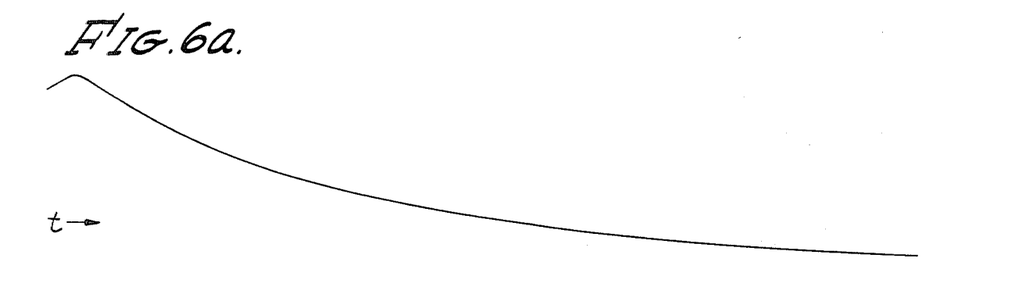
FIGS. 6a-6e illustrates the waveforms obtainable through use of the system shown in FIG. 1.
Figure 6B:
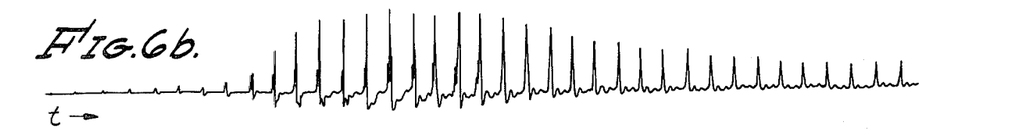
Figure 6C:
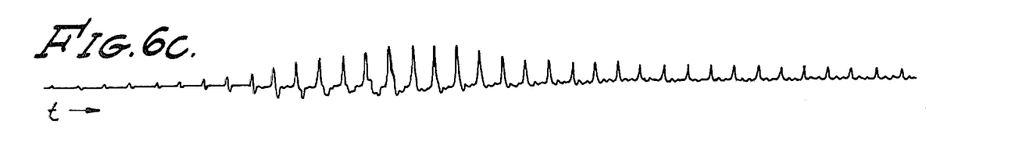
Figure 6D:
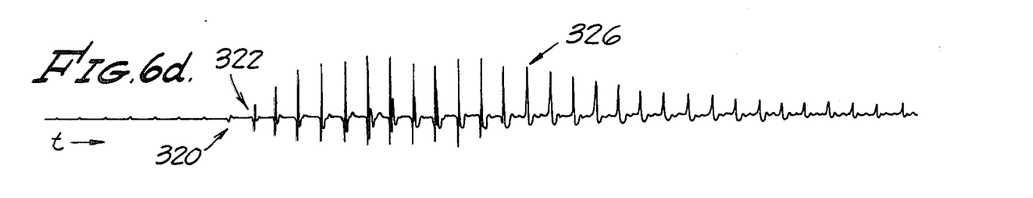
Figure 6E:
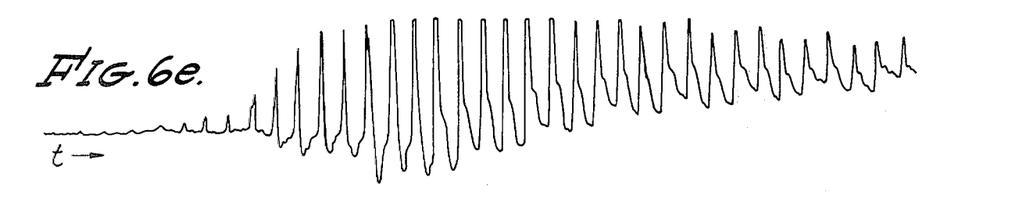

FIGS. 6a–6e show the various waveforms which are associated with the dual sensing element transducer of FIGS. 2a–c, as recorded on a stripchart recorder. More particularly, FIG. 6a shows the air pressure in the cuff 10 during a portion of the inflation cycle and the deflation cycle. FIG. 6b reflects the waveform detected by the sensing element 120a which is contiguous to the subject's brachial artery, while FIG. 6c reflects the waveform detected by the outboard sensor 120b. FIG. 6d shows the differential waveform which results from subtracting the waveform of FIG. 6c from that of FIG. 6b. FIG. 6e shows the integral of the waveform of FIG. 6b.

Referring first to FIG. 6b, the waveform produced by the sensing element 120a of the transducer 30 can be better appreciated. During a period when the subject's artery is at least partially occluded, each heartbeat is reflected at the point of occlusion by a series of pressure waves. The pressure waves are transformed by the transducer sensing elements into a corresponding series of pulses as shown in FIG. 6b. By comparing the cuff pressure shown in FIG. 6a with the occurrence of the pulses in FIG. 6b, the pressure at the time of each pulse can be determined.

The pulses of the waveform shown in FIG. 6c, associated with sensing element 120b nearest the cuff 10, can be seen generally to be of a smaller amplitude than those associated with the sensing element 120a, and do not in all instances reflect each of the components of the waveform in FIG. 6b. However, the pulses in FIG. 6c can be seen to correspond in many respects to the pulses of FIG. 6b. Because of this correspondence, the waveform shown in FIG. 6d is of significance.

FIG. 6d, as noted above, shows the differential waveform which results from subtracting the waveform of FIG. 6c from that of FIG. 6b. The result is that those components which are common to both FIG. 6b and FIG. 6c are eliminated, thereby eliminating numerous artifact signals and other noise. Also, it will be appreciated from a careful examination of FIG. 6d that elimination of common mode signals causes the initial pulses to be made more distinct. The result is that the waveform of FIG. 6d is readily susceptible of accumulation and analysis by the control apparatus 40.

FIG. 6e, which shows an integration of the waveform of FIG. 6b, can also be seen to provide useful information, and also to correspond substantially to the arterial waveforms associated with intra-arterial catheters. The waveform shown in FIG. 6e is helpful in determining mean arterial pressure, and may also be useful for determining other cardiovascular characteristics which heretofore could only be determined by invasive techniques. It will thus be appreciated that the transducer of the present invention provides substantial improvement over those of the prior art, and provides significantly improved information for analysis by the control apparatus 40.

In addition to knowing the cuff pressure at the time of each event shown in FIGS. 6b–6e, it is also useful to know the time of each such occurrence, and the amplitude of each pulse. Each of these may be readily ascertained with the control apparatus 40 of the present invention and, as will be discussed shortly, these parameters permit the desired characteristics of the subject's cardiovascular system to be determined.

Nearly all of the events, representing heartbeats, shown in FIGS. 6b–6e can be seen to be comprised of a plurality of pulses, some of a positive polarity, and some negative. It will be appreciated that the choice of polarities is arbitrary and does not affect the operation of the present invention. Because each pulse appears to have significance in analyzing the cardiovascular condition of the subject, each pulse must be recorded.

However, inherent in any analog system, and particularly for analog interfaces with mobile subjects, are difficulties with noise. Noise, or unwanted signals, manifests as small pulses, erratic pulses, or high frequency pulses and can lead to significant error if not eliminated from the data received from the transducer. Since most noise signals are of relatively low magnitude, many of the unwanted signals from the transducer can be eliminated by establishing a signal threshold, and screening out those signals which do not exceed the threshold. This is one of the functions accomplished by the control apparatus 40 as discussed in greater detail in connection with FIG. 3.

Figure 3:
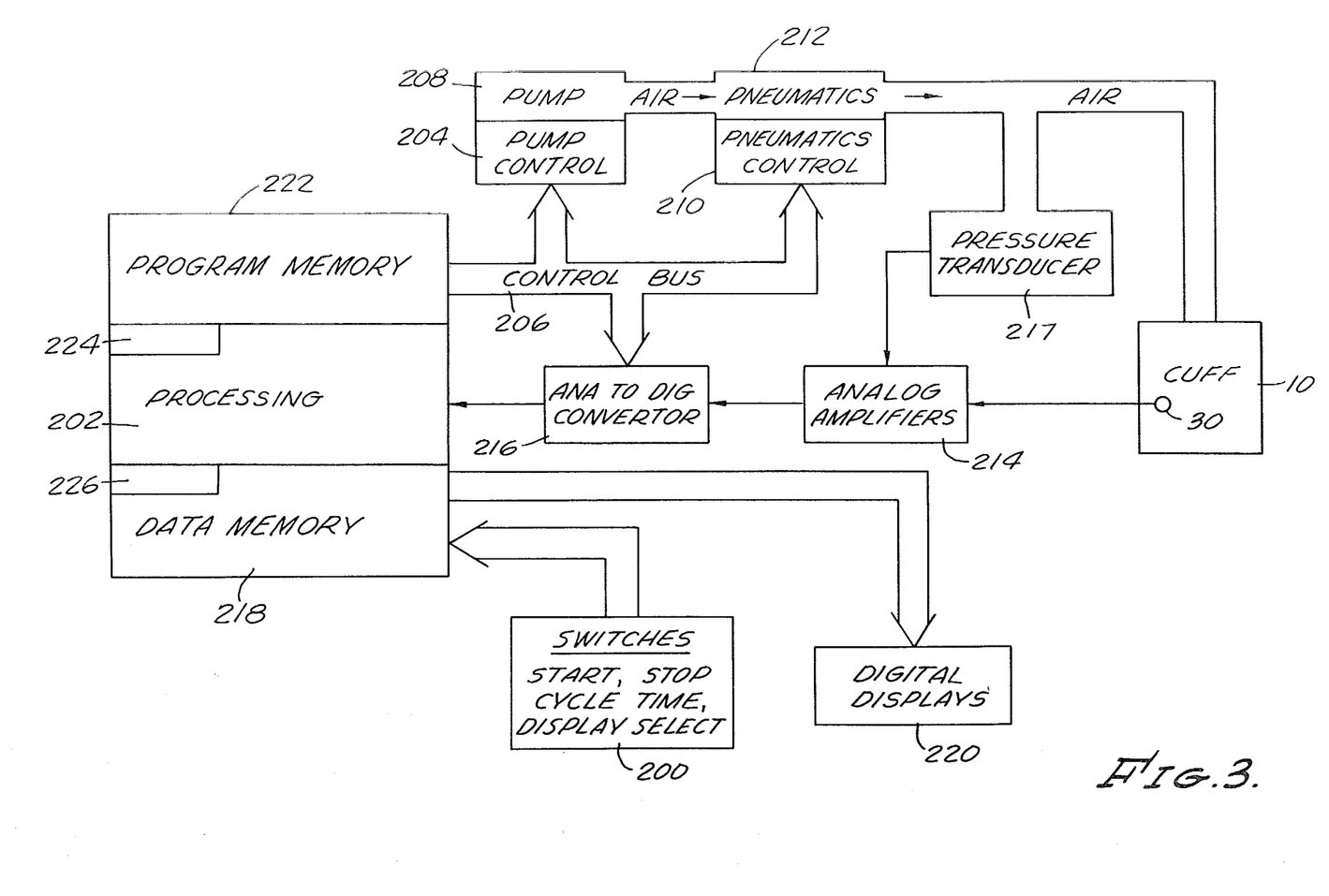
FIG. 3 illustrates the control portion of the system shown in FIG. 1.
Figure 4:
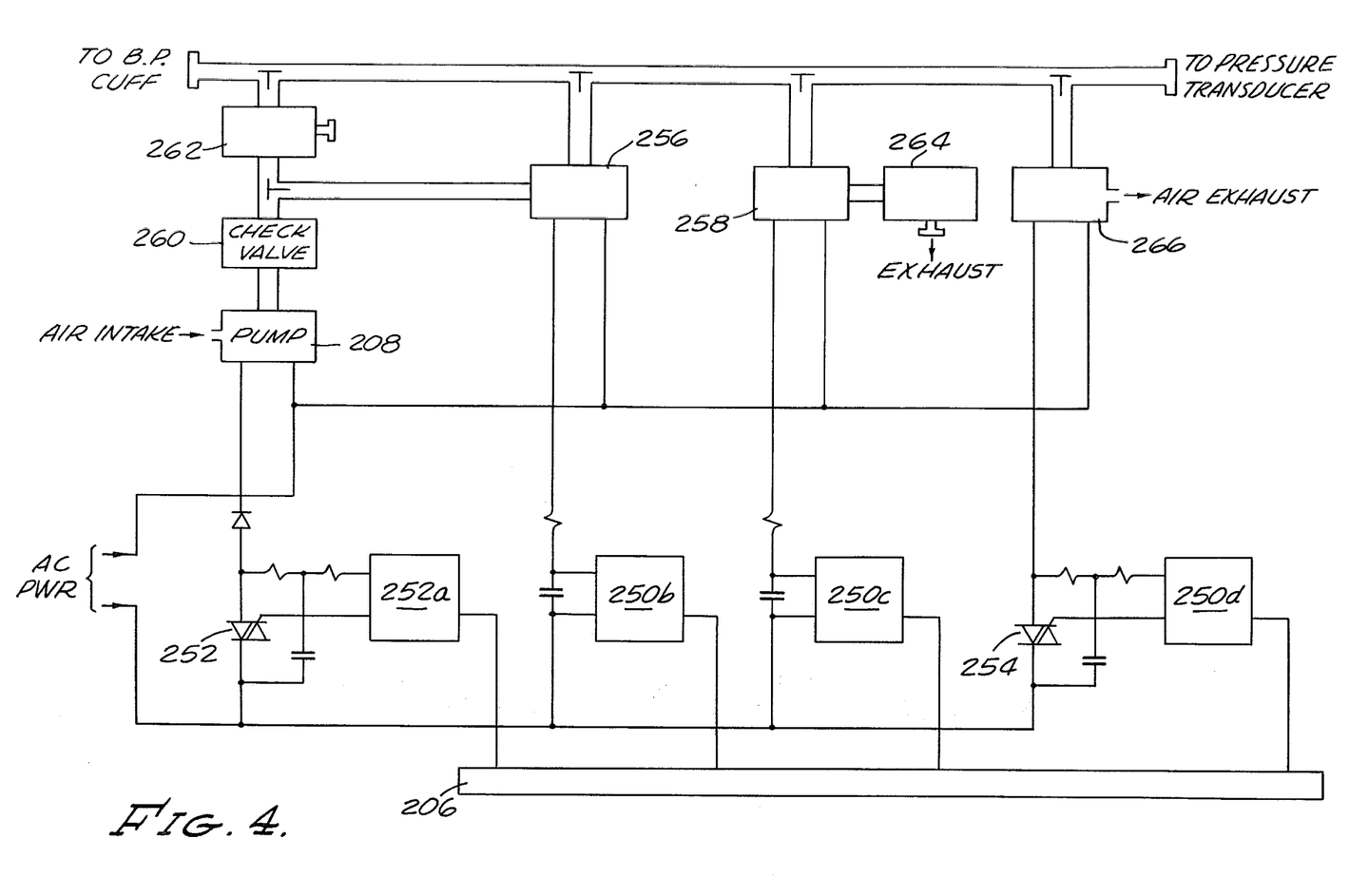
FIG. 4 illustrates the pneumatic portion of the system shown in FIG. 1.

The control apparatus 40 shown in FIG. 3 includes, generally, a data handling portion and a pneumatics control portion. The data handling portion may further be broken down into a data accumulation portion, and an overlapping data analysis portion. However, before treating each of these portions in detail, a brief description of the general operating characteristics of the control apparatus of FIG. 3 may be useful.

Once the cuff 10 is properly affixed to the subject, the control apparatus is activated by means of switches 200, which cause the system to start operating. On startup, a processing device 202 signals a pump control circuit 204 via a control bus 206. The signal causes the pump control circuit 204 to begin operating an air pump 208. At the same time as the start signal from the processing device 202 causes operation of the pump 208 to begin, the processing device 202 supplies a signal via the control bus 206 to initialize a pneumatics control circuit 210. The pneumatics control circuit 210 operates a pneumatics section 212, comprising a plurality of valves and the like described in detail in connection with FIG. 4, to direct air from the pump 208 into the cuff 10, thereby beginning inflation.

During inflation of the cuff, various Korotkoff sounds are detected by the transducer 30. These sounds are converted to electrical signals and conveyed to a plurality of analog amplifiers 214 where the signals are amplified and supplied to an analog to digital converter 216. The analog to digital converter supplies signals to the processing device 202 to determine if the cuff is inflated sufficiently in accordance with a criteria set out in general terms in U.S. Pat. No. 4,058,117, but utilizing a significantly different structure as discussed in connection with FIG. 4. The cuff pressure is indicated, where necessary, by a pressure transducer 217, which provides a signal to the analog amplifiers 214 as discussed above.

After the cuff 10 has been suitably inflated and the artery being monitored is fully occluded, the processing device 202 transmits a signal via the control bus 206 to stop the pump. The processing device 202 simultaneously transmits to the pneumatics portion a signal which opens a cuff bleed valve, thereby beginning deflation of the cuff 10. As the cuff deflates, Korotkoff sounds are again detected by the transducer 10 and transmitted to the processing device 202. Once the amplitude of the detected pulses exceeds the noise threshold discussed above, the signals are stored in a data memory 218. Each pulse is represented by a criteria discussed in detail hereinafter.

Eventually all of the pulses above the noise threshold generated by the transducer during deflation of the cuff are recorded, and the processing device 202 signals the pneumatics control circuit 210 and pneumatics portion 212 to dump the remaining pressuring in the cuff, and the data analysis portion begins. After evaluating the data in accordance with a criteria discussed in detail hereinafter, the cardiovascular characteristics under test are displayed on displays 220, which may for example be a digital display.

With the foregoing general description of the control apparatus shown in FIG. 3, a detailed discussion of the apparatus may be understood beginning with the start of the deflation of the cuff 10. As the cuff deflates, the transducer 30 begins detecting Korotkoff sounds from the occluded artery, and transmits those sounds as analog signals to the analog amplifier 214. The analog amplifiers 214 provide a differential output of the signals provided by the sensing elements 120a-b, and may also be configured to supply an output which is the integral of the transducer signals. In addition, the amplifiers 214 provide an output indicative of the pressure detected by the pressure transducer 217.

These analog signals are then supplied to an analog-to-digital converter 216, which converts the analog arterial waveform into a binary format for processing by the processing device 202. The analog to digital converter 202 may, for example, be a ten bit A/D converter wherein there are nine bits of resolution plus one polarity bit. It should be noted that the data also may be obtained in an analog manner, as by the use of peak detectors and sample and hold circuitry. The processing device 202 may be either a microprocessor such as the Texas Instruments TMS 9900 device, or may be implemented with dedicated logic circuitry. Other suitable microprocessors are likewise available from many of the semi-conductor manufacturers. In the event a microprocessor embodiment is chosen, a program memory 222 may be included with the processing device 202, and fixes the function and operation of the device 202 in much the same manner as if dedicated logic circuitry had been used. The program memory 222 may be a ROM (read only memory) such as the Texas Instruments TMS 2708 or other suitable device. A master clock 224, such as the Texas Instruments TIM 9904 or other suitable device, is also required although in many devices such a clock is integral with the processing device.

The processing device 202 and program memory 222 combine to implement a data accumulation method or procedure as well as a data analysis method or procedure. The data accumulation procedure is implemented first, and causes selected ones of the digitized transducer signals to be stored in the data memory 218, which may be either a network of registers, a RAM (random access memory), or other suitable means.

The data accumulation procedure, in simplest terms, involves examining a sequential sampling of the transducer signals, making a preliminary determination of the validity of the sampled data, and then determining whether the data sample indicates the occurrence of a transition. If the data is determined to be valid and also indicates a transition as discussed hereinafter, the data sample is stored. To ensure that the data samples are taken frequently enough to reflect changes in the waveform, the sampling rate should be significantly greater than the heartrate of the subject. A sample rate of two milliseconds may, for example, be used.

As noted above, the first step in the data accumulation procedure is to determine, at least preliminarily, the validity of the data. To accomplish this, a noise threshold is established and is preset into the memory 218. Since the transducer signals can be bipolar, the noise threshold should likewise be bipolar. Although the magnitude of the threshold is somewhat arbitrary, and suitable threshold levels vary over a wide range, a suitable threshold may for example be two percent of the maximum signal. More particularly, if the maximum signal is 512, a suitable threshold might be ten.

If the digitized transducer signal exceeds the noise threshold, it is further examined by the processing device 202 to determine if the data sample represents a transition and should thus be stored in the data memory. To facilitate such determination, each data sample is temporarily stored in a scratchpad memory 226, which may for example be a partition of the date memory 218. The temporarily stored data sample is then compared with the next data sample, and if the comparison indicates a transition has occurred, the appropriate sample is stored in the data memory 218. To ensure that only data from the current test is stored, the memory 218 is initialized to all zeroes when cuff inflation begins.

Figure 7:
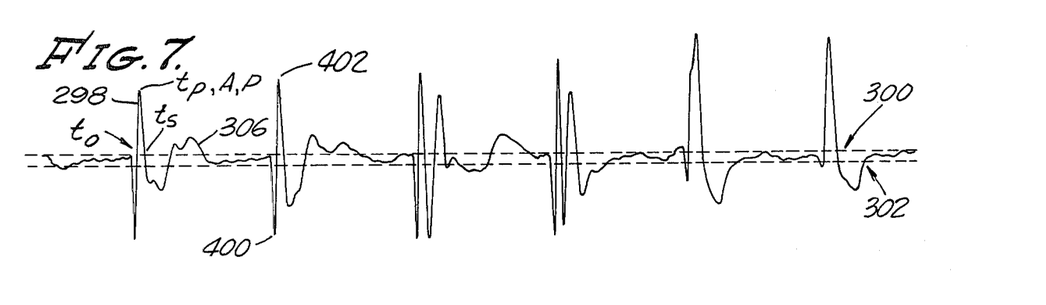
FIG. 7 shows an expanded version of FIG. 6d.

To better appreciate the transitions which cause a data sample to be stored in the data memory 218, reference is made to FIG. 7, which is essentially a reproduction of the waveform of FIG. 6d on an expanded time scale; i.e., an increased chart speed on the strip chart recorder. From examining the waveform shown in FIG. 7, it can be determined that each pulse, for example a pulse 298, within the cluster of pulses representing a hearbeat, exceeds either the positive noise threshold 300 or negative noise threshold 302, reaches a peak, and then recedes below the threshold. Some of the pulses such as a pulse 306, may also reach a peak, recede without going below the threshold, increase to a second peak, and finally recede to below the threshold. The significant characteristics of each such pulse have been found to be the time ($t_o$) at which the pulse initially exceeds the threshold, the time at which the pulse reached a peak ($t_p$) as well as the amplitude of the pulse (A) and the cuff pressure (P) at that moment, and finally the time ($t_s$) at which the pulse fell below the threshold. Time indications are provided by the master clock 224.

Thus each pulse having a single peak can be identified by five parameters: $t_o$, $t_p$, A, P and $t_s$. Pulses having more than one peak can be defined by $t_o$, $t_s$ and a set of ($t_p$, A and P) for each peak exhibited by the pulse. The amplitude measurement, A, as noted before, includes an indication of polarity. As previously noted, the data sampling rate of the present invention is significantly greater than the rate at which pulses occur, and thus several data samples will be taken during the occurrence of each pulse.

In accordance with the present invention, the processing device 202 compares each valid sample to the last previous sample. If the last previous sample was not valid, (i.e., the pulse amplitude was less than the noise threshold), the current sample is necessarily the first valid sample to exceed the threshold, and is thererfore to be recorded in the data memory 218. Invalid prior samples may be indicated by entering all zeroes into the scratchpad memory 226, although other indicator arrangements are suitable. While only the time ($t_o$) at which the pulse exceeded the threshold is recorded in the data memory 210, the time, amplitude and cuff pressure of the sample are stored in the scratchpad memory 226.

Each subsequent, valid data sample is then compared with the data sample stored temporarily in the memory 214. If the absolute value of the amplitude of the new sample exceeds the amplitude of the previous sample, no transition has occurred and the new sample replaces the previous sample in the temporary memory 226 without causing the previous sample to be stored in the data memory 218, i.e., the previous sample is lost. However, if the new sample has an absolute amplitude less than the preceding sample, the previous sample indicates a peak in the pulse, and is stored in the data memory 210. The new sample, however, replaces the old sample in the temporary memory 214.

Thereafter, the amplitude of the data samples decreases until at some point the current data sample is either invalid for being below the threshold or increases in amplitude relative to the preceding sample. If the data sample is invalid, the time ($t_s$) of the sample is stored in the data memory 210; if the current sample increased in amplitude, the previous sample is stored in the data memory 210. In either event the current sample replaces the previous sample in the register 214. Throughout the sampling period the cuff pressure is decreasing as a result of the bleed valve discussed briefly in connection with FIGS. 1 and 3 and more particularly discussed in connection with FIG. 4.

Eventually the amplitudes of the data samples reduce to a point where no sample exceeds the threshold for a period of time (which is preset into the processing device 202), or the cuff pressure reduces to a minimum, thereby causing the processing device 202 to terminate sampling of the transducer waveform. This marks the end of the data accumulation procedure, and each of the valid pulses received from the transducer 30 is now represented in the digital data stored in the data memory 210. It will be appreciated by those skilled in the art that each data sample, of each valid data sample, could have been stored in the data memory 210 without departing from the spirit of the present invention; however, such a technique requires considerably more memory space than is needed for the data accumulation procedure described above. Likewise, more rapid access can be obtained with a smaller memory, resulting in more efficient operation.

Following completion of the data accumulation procedure, the processing device 202 begins the data analysis procedure to determine the selected cardio-vascular characteristics. Typically, heart rate may be analyzed together with systolic, diastolic and mean arterial pressures. Various other characteristics, such as valve closure times and carotid upstroke times, and various arrythmias and abnormal cardiovascular conditions, also appear determinable. However, before determination of specific parameters is discussed, it is helpful for the elimination of artifacts to establish some reference criteria for use in subsequent analysis.

Initially, an arbitrary time window may be established, setting forth minimum and maximum times between when a subsequent pulse must occur for the preceding pulse to be considered valid. It has been found that an acceptable minimum time is on the order of 250 ms, while an acceptable maximum time is on the order of 2000 ms. Thus, for a stored pulse to be considered valid, a subsequent stored pulse must have occurred between 250 and 2000 milliseconds later.

The references are established in a plurality of steps. First, the data stored in the memory 210 is scanned to isolate a predetermined number of pulses having the largest amplitudes of a selected polarity. As noted before, polarity is also selected arbitrarily, and for purposes of this example, positive polarity pulses will be examined. Although the exact number of pulses isolated may vary over a wide range, particularly with variations in cuff bleed rate, use of the four greatest amplitude pulses as shown, for example, in FIG. 6d has been found acceptable.

After the largest amplitude pulses have been determined, the average of the amplitudes of those pulses is obtained, and a reference level of fifty percent of the average is used. The remaining data is then scanned to isolate those positive pulses which meet the minimum/maximum time criteria set forth above and also exceed the reference level. Depending upon cuff bleed rates, several pulses will exist which exceed the reference levels; however if the cuff bleed rate is too high, it may be necessary to use fewer pulses. If the cuff bleed rate is matched to the number of pulses, the data should not be considered valid unless a suitable number of data pulses in excess of the threshold exist. For example, with a cuff bleed rate of three millimeters of mercury per second, at least four pulses in excess of the reference level should exist for valid data. In most samples, such as that shown in FIG. 6d, there are far more pulses which meet the above criteria than are deemed necessary to consider the data valid. Thus the criteria permits monitoring of patients with irregular heartbeats or other cardiovascular difficulties.

After it is established that the stored pulses reflect a valid test of the subject, average heart rate may be determined. Because the pulses which meet the amplitude and time criteria set forth above are typically the first pulses in each cluster of pulses that represents a heartbeat, average period between beats may be determined simply by totaling the elapsed time between the first and last pulses meeting the above criteria and then dividing that time by the total number of pulses which met the criteria. Once the average total between beats is determined, average heart rate may be easily determined simply by dividing the average period into one minute.

Also, period deviations tailored to the heart rate of the specific individual being monitored may be determined by use of the average period between heartbeats. It has been found that the time between beats in a normal subject may vary by as much as ±25%; however it will be recognized by those skilled in the art that the variations is not critical, but may be varied over a significant range while still yielding acceptable results in subsequent analysis.

By use of the foregoing procedures, which comprise a significant part of the present invention, determination of systolic pressure is made straightforward. As discussed previously, the pressure waveform deteted by the transducer 30 (FIG. 1) is believed to be comprised, during partial occlusion, of a laminar flow component together with a turbulent component. More specifically, when the cuff pressure is slightly below that necessary for full occlusion, the pressure head developed by the heartbeat causes the artery to dilate slightly. This permits a small amount of blood to flow through the artery in what is believed to be a turbulent flow, much the same as venturi. As cuff pressure decreases, the artery is continually open at least partially, leading to what is believed at present to be both turbulent and laminar flow. Once the artery is no longer occluded, flow becomes substantially laminar. The transition from primarily turbulent to primarily laminar flow may be regarded as the acoustical diastolic pulse, and will be discussed hereinafter.

In keeping with the above, systolic blood pressure, which may be regarded as the highest cuff pressure at which a heartbeat causes blood to flow in the artery, and is thus the onset of turbulent flow, may be determined by the processing device 202 since, for the embodiment disclosed herein, turbulent flow is detected as a negative pulse. By scanning the data stored in the memory 218 to determine the first negative polarity pulse of the differential waveform (FIG. 6d) which exceeds the noise threshold 302 (shown in FIG. 7) and which is followed by a heartbeat meeting the time zone criteria described above, the systolic pulse may be isolated. Thus the pulse 320 in FIG. 6d may be regarded as the systolic pulse, depending upon the threshold set for the particular application, since it appears to exceed the threshold and is followed by a heartbeat 322 meeting the timing criteria. The systolic pressure may readily be determined by comparing the cuff pressure from FIG. 6a with the time of occurrence of the systolic pulse 320. As noted previously, all of such timing information is stored in the data memory 218 during the data accumulation period.

It should be noted that accurate determination of systolic pressure with the present invention depends to some extent upon cuff bleed rate. Because the pulse which indicates the beginning of blood flow in the artery (systole) is generally of relatively small magnitude, the data sample may be just below the threshold at the sample. However, a cuff bleed rate which is suitable for use during the remainder of the sampling period (such as three millimeters of mercury per second) may cause the cuff to deflate so quickly that it is well below actual systolic pressure by the occurrence of the next heartbeat, which is the next time meaningful samples may be taken. This limitation may be solved by causing the cuff bleed rate to be slower during the initial period than thereafter. For example, a suitable initial bleed rate may be only one- half or one millimeter of mercury per second. Alternatively, deflation of the cuff may be temporarily halted by the processing device 202 once a potential systolic pulse is detected, thereby permitting further samples to be taken during the next heart beat.

Determination of a subject's diastolic blood pressure with the waveform analysis device 40 is somewhat more complex. At present, it is believed that the present invention can provide a display of diastolic blood pressure compatible with either the stethoscope and sphygmamonometer approach, or the intra-arterial catheter approach. Each approach will be treated in the following discussion.

As is apparent from a review of FIGS. 6b–e and 7, a typical heartbeat presents an initially negative-going pulse followed by a positive-going pulse (a negative-positive pulse pair), followed by a string of other pulses which may be either positive or negative going. It has been found that diastolic blood pressure can be reliably determined for intra-arterial catheter compatability by monitoring the occurrence of negative-positive pulse pairs which meet the time zone criteria discussed above. Thus a sort procedure is used by the processing device 202 in scanning the data stored in the data memory 218. Beginning with the systolic pulse, detection of which is described above, the time zone criteria is applied and the stored data is scanned in the direction of increasing time. The time zone is preferably measured from the clock value of the first positive pulse occurring during the time zone, although other reference points are acceptable. By use of the time zone criteria any pulses outside of the zones are eliminated from consideration here, thereby avoiding problems with ringing signals as shown in FIG. 6d, although these additional pulses may be later used in isolating other cardiovascular characteristics.

If the scan of the stored data reflects that a negative-positive pulse pair occurred meeting the time zone criteria, the absolute values of the pulse pair are added together and stoed in the data memory 218 along with the pressure coincident with the positive pulse of the pulse pair. In the event more than one pulse pair occurs during the time zone, the pulse pair having the largest sum of absolute values is stored and the remaining pulse pairs discarded. In this manner each heartbeat is resolved into a single negative-positive pulse pair for purposes of calculating diastolic pressure.

In some instances, a negative-positive pulse pair will not occur during the time zone although the data is in fact valid. In such instances the absolute value of the largest amplitude pulse is stored, along with its coincident pressure. In other instances, no pulses at all will occur during the time zone—that is, the heart will skip a beat. In the event a skipped beat is detected (by its absence) the processing device 202 extends its scan for one additional time zone. If no pulse occurs during the additional time zone, subequent data is presumed invalid and the scan is terminated. However, in most instances a beat will occur during the extended time zone, and its representative pulse pair stored as above. The time zones continue to be applied until either there is no more data in the memory 218, or the second extension of the time zone yields no pulses.

Once all of the pulse pair and single pulse sums are stored as a Sort List in the memory 218, the Sort List is scanned and, for example, the four largest pulses are located. From the average of these pules a reference level is established at, for example, fifty percent of the average. Using this reference level, selection is begun of pulses for determination of diastolic blood pressure.

The processing device 202 then rescans the data to ensure that the analysis for determining diastolic pressure begins on the declining portion of the waveform shown in FIGS. 6b–6d. This may be accomplished in either of two ways: first, the processing device 202 can be configured to begin scanning part way through the data, for example one-third of the way through; or second the device 202 can look at only those pulses which follow the largest amplitude pulse. For most applications the first method for locating the declining portion of the waveform is preferred. The range of acceptable beginning points for the first method may be permitted to vary over a relatively wide range to still yield acceptable results, as those skilled in the art will appreciate.

Whichever method is used as a beginning point for scanning the data, the processing device 202 then reexamines the data to locate a plurality of pulses which are below the reference and within a predetermined amplitude range of each other. While the number of pulses and the relative range therebetween is subject to substantial variation, exemplary values for such parameters are on the order of three pulses below the reference with an initial variation of no more than twenty-five percent. Thus, for the exemplary values above, the processing device 202 would scan the stored data to locate three pulses with amplitudes which are within twenty-five percent of one another.

If three such pulses can be located, the processing device then incrementally reduces the range of permissible variation, and searches again to ascertain whether three pulses exist which meet the revised criteria. While the increment size may be varied, a suitable increment has been found to be one percent (i.e., a reduction from 25% to 24%). If three suitable pulses are again found, the range is again incrementally reduced; this process continues in iterative fashion until either three suitable pulses cannot be found, or until a minimum range of variation is reached. Again, the minimum range of variation is itself subject to variation but a suitable minimum is on the order of ten percent. The minimum range of variation cannot be reduced to zero because subdiastolic signals, which can be received by the transducer of the present invention, could then be mistakenly included in the calculation of diastolic pressure.

Diastolic pressure, for compatibility with intra-arterial catheters, is equal to the cuff pressure when three pulses are found at the lowest range of variation, whether the range occurs at ten percent, twenty-five percent, or in between. However, for some subjects, three pulses will not exist within even a twenty-five percent range. In such cases the last valid pulse below the reference level may be selected as representing diastolic pressure, although alternative criteria will be apparent to those skilled in the art, given the teachings herein. If no valid pulses exist below the reference value, an error flag is set; however, since the reference value is substantially arbitary, many alternatives exist for identifying diastolic pressure in unusual cases.

As noted previously, the present invention may also be configured to provide diastolic blood pressure readings compatible with those obtained by the stethoscope and sphygomomanometer approach. It has been determined empirically that the diastolic pressure as determined by the sphygomanometer approach corresponds with the near or complete disappearance of the initial negative pulses detected by the transducer of the present invention. As noted above, negative pulses corresponds, for the embodiment disclosed herein, with the pulses which result from turbulent blood flow. Thus, for example, the stethoscope-sphygmomanometer diastolic pressure for the waveform of FIG. 6d occurs approximately with the pulse 326. The processing device 202 can thus determine diastolic pressure in a manner which non-invasively provides highly repeatable indications of blood pressure which are compatible with both of the common techniques.

Although the data accumulation and data analysis procedures described hereinbefore are set forth with data analysis following data accumulation, it is also possible to use real time processing for the data analysis procedure without department from the present invention. In the event real time processing is used, it may be desirable to include in the pneumatics portion of the system of the present invention means for dumping the cuff pressure once the diastolic pressure has been determined, in addition to the provisions for dumping cuff pressure discussed previously.

The system of the present invention also provides an indication of mean arterial pressure. By integrating the waveform of FIG. 6b after diastolic pressuere has been reached (as shown in FIG. 6e), mean arterial pressure is determined by calibrating the integrated waveform according to the systolic and diastolic pressures determined above. The resulting waveform is then divided by the pulse period, also determined above, to yield mean arterial pressure. It will be appreciated that mean arterial pressure may be determined in accordance with this procedure as part of a continuous monitoring technique discussed hereinafter. It is also to be noted that the waveform of FIG. 6e corresponds closely to the waveform produced by an intra-arterial catheter; however the waveform of FIG. 6b appears at present to provide more information than the waveform of FIG. 6e.

Although the procedure during the pump up phase is substantially as described in U.S. Pat. No. 4,058,117, the pneumatics portion of the system of the present invention varies in certain aspects from the device disclosed there. The differences of the present invention can be appreciated from FIG. 4, which illustrates in detail the pump control circuit 204, pump 208, pneumatics control circuit 210 and pneumatics 212 shown in FIG. 3. More specifically, the control bus 206 supplies individual control signals to a plurality of triac drivers 250a—d, which may for example be a Motorola type MOC 3011 device. The triac drivers 250a and 250d in turn control their associated triacs and biasing circuitry 252 and 254 in a conventional manner. Triac drivers 250b and 250c directly control solenoid controlled bypass valves 256 and 258, which may for example by Richdel type R702 devices. When the system of FIG. 1 is initially started by activation of the switches 200, the processing device 202 causes the triac drivers 250a and 250b to be actuated.

The traic driver 250a and its associated triac 252, shown in FIG. 3 as the pump control circuit 204, control the air pump 208 and when actuated cause the pump to begin inflation of the cuff 10 through a check valve 260, a needle valve 256. Because the valve 256 allows a relatively large volume of air to enter the cuff 10, initial inflation proceeds rapidly. However, once the cuff pressure approaches the beginning of the systolic range, for example 100 mm Hg as monitored by the pressure transducer 232, the processing device 202 deactivates the triac driver 250b, thereby closing off the bypass valve 256.

This leaves only the needle valve 262 to supply air to the cuff, and thus inflation proceeds more slowly. In this manner cuff inflation is carefully monitored and may be terminated without excessive inflation after complete occlusion is indicated by the cessation of Korotkoff sounds. Inflation is terminated by the absence of detected signals from the transducer 30 for a period of time, such as three seconds, or by a predetermined pressure in excess of the pressure at which Korotkoff sounds ceased, or by the pressure transducer 217 indicating that a predetermined maximum cuff pressure, for example 250 mm Hg, has been reached, in either case the processing device 204 deactivates the pump 208.

Once the pump 208 is deactivated and inflation stops, the processing device 202 activates the traic driver 250c, which opens the solenoid controlled bleed valve 258. The bleed valve 258 feeds air to a needle valve 264 which slowly exhausts the air from the cuff 10 to the atmosphere. A typical bleed rate may, for example, be three millimeters of mercury per second. However, in certain situations a slower bleed rate may be preferred. As mentioned above, during the initial bleed stage when cuff pressures are approaching systolic pressure, the bleed rate may be advantageously reduced to enhance accuracy in detecting the first valid pulse. A typical reduced bleed rate would be on the order of one-half to one millimeter of mercury per second. Such a reduced bleed rate could be implemented by a second triac driver, bleed valve and smaller size needle valve in addition to the triac driver 250c, bleed valve 258 and needle valve 264. For example, the additional needle valve could be designed to provide the reduced flow until the systolic pulse is detected, whereupon the needle valve 264 is opened to increase flow to the higher rates. A wide range of acceptable bleed rates will be apparent from the discussion herein.

After the pressure in the cuff 10 is evacuated through the needle valve 258 to a relatively low cuff pressure, such as forty millimeters of mercury, the processing device 204 signals the triac driver 250d to actuate a dump valve 266. Actuation of the dump valve 266 reduces the cuff pressure to atmospheric. The dump valve 266 may also be actuated if no valid pulses are detected for a predetermined period during deflation, for example three seconds.

The transducer 30 of the present invention may also be employed to provide a continuous display of a subject's arterial waveform. To accomplish this, the cuff 10 (FIG. 1) and transducer 30 are positioned as before, but the cuff is inflated to a pressure which is sub-diastolic but which still ensures good contact between the transducer and the subject. Since vascular waveforms need not be monitored solely from arteries, the transducer 30 may be positioned near a vein and the cuff inflated to a suitable sub-venous pressure.

The signals provided by the transducer 30 may then be supplied to a continuous display device such as an oscilloscope, or may be supplied to a waveform analysis device such as the control apparatus 40 of the present invention. In either event, the waveforms may be calibrated through use of the systolic and diastolic blood pressure values determined above.

Figure 5A:
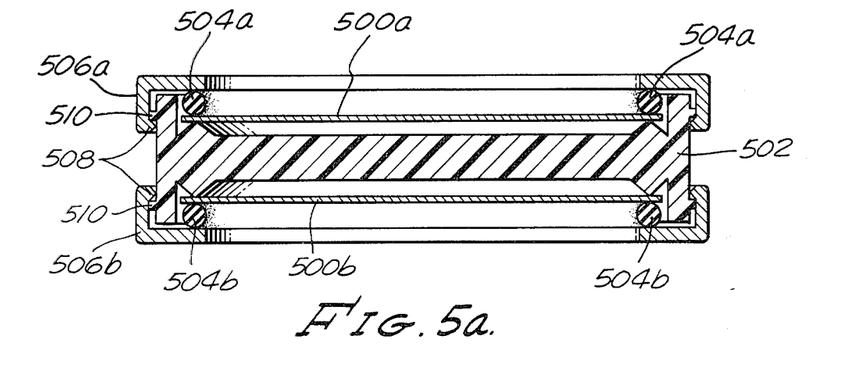
FIGS. 5a-5c each illustrate alternatives to the transducer shown in FIGS. 2a-2c.
Figure 5B:
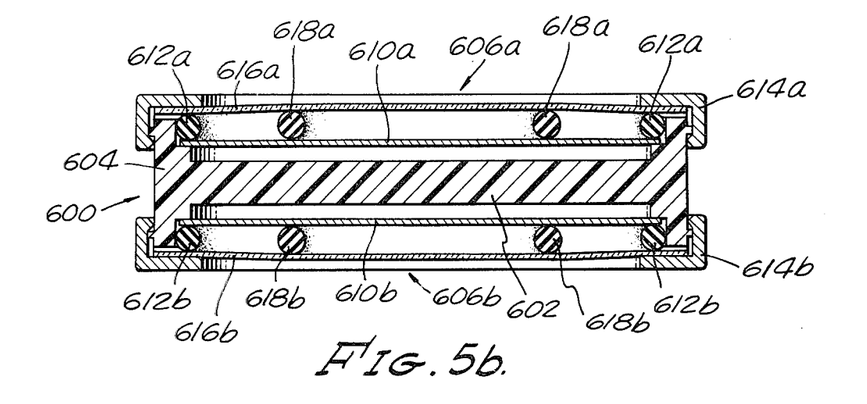
Figure 5C:
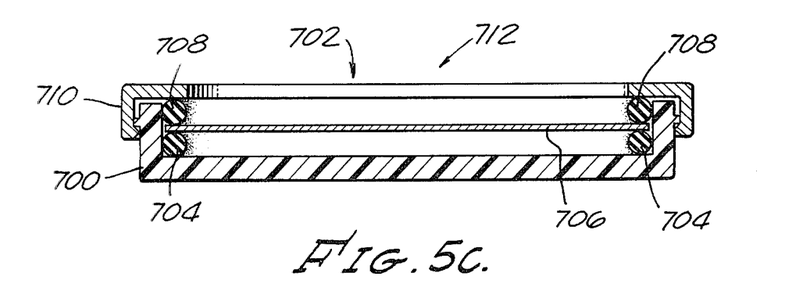

In addition to the transducer shown in FIGS. 2a-2c, various alternative embodiments may also be used with the present invention and are shown in cross-section in FIGS. 5a-5c. FIG. 5a illustrates a transducer substantially identical with that shown in FIGS. 2a-2c, including a pair of sensing elements 500a-b which are fixed at their outer peripheries within a housing 502 by means of O-rings 504a-b. However, unlike the transducer of FIGS. 2a-c, the O-rings 504a-b are retained within the housing 502 by means of press fit caps 506a-b. The caps 506a-b may be machined or molded to include a locking ridge 508 on the interior surface thereof, which tightly interlocks with corresponding ridges 510 on the housing 502. The tolerances of the housing 502 and caps 506a-b must be such that the caps, when affixed to the housing 502, fixedly locate the sensing elements 500a-b between the housing 502 and O-rings 504a-b. It will be appreciated that each cap 506a-b includes an orifice therethrough of the same type as the caps 10 in FIGS. 2a-2c, and the remaining cavity may be filled with a suitably low viscosity rubber such as described previously.

FIG. 5b illustrates yet another alternative to the transducer of FIGS. 2a-c. More particularly, a housing 600 has a central plate 602 and a cylindrical outer wall 604 which together form a symmetric pair of cavities 606a and 606b. The cylindrical wall 604 forms a pair of ledges 608a and 608b, on which rest a pair of sensing elements 610a and 610b. The sensing elements 610a-b are retained in position by O-rings 612a and 612b, respectively, which are in turn maintained in position by a pair of caps 614a and 614b, respectively. While the caps 614a-b are shown as retained by a press fit as shown in FIG. 5a, it will be appreciated that threaded caps as shown in FIGS. 2a-c may also be used.

The O-rings 612a-b may be deformable so as to deform about the edges of the sensing elements 610a-b, thereby fixing the lateral position of the sensing elements 610a-b and causing the sensing elements to be fixedly supported at their peripheries. As with the transducers of FIGS. 2a-c and 5a, the caps 614a-b have an orifice therethrough. In the case of the transducer of FIG. 5b, however, the orifices are enclosed by a sheet of flexible plastic or other suitable material 616a-b which is affixed between the housing 600 and the caps 614a-b. The sheets of material 616a-b permit a second, smaller diameter O-ring 618a-b to be located between the sheets 616a-b and the sensing elements 610a-b, thereby providing increased transmission of pressure waves to the sensing elements 610a-b. The diameter of the second O-rings 618a-b may be varied substantially depending upon the transmission characteristics desired. The remaining portions of the cavities 606a-b may be filled with a suitable rubber or other material if desired. It will be appreciated that the alternative transducers of FIGS. 2a-c and FIGS. 5a-c differ primarily in a trade-off between sensitivity and linearity. The embodiment of FIG. 5b is in some respects less sensitive than the device of FIGS. 2a-c, but has higher immunity to motion artifacts. Thus different embodiments may be preferred for different applications.

Although each of the transducers discussed herein have been of the double sensing element type, which in itself provides particularly unexpected results, many of the features of the remaining portions of the present invention may be achieved by use of a single sensing element tranducer as shown in FIG. 5c. As noted previously, the single sensing element transducer cannot provide the differential waveform shown in FIG. 6d. The signals produced by each of these transducers will preferably be matched to a relatively low impedance device, to avoid inadvertent integration which may result from an RC time constant which may be associated with a high input impedance.

In the particular embodiment shown in FIG. 5c, a housing 700 forms a cylindrical cavity 702 in which an O-ring 704 rests. The diameter of the O-ring 704 is substantially the same as the diameter of the cavity 702, thereby supporting a sensing element 706 substantially at the outer periphery thereof. Above the sensing element 706 rests a second O-ring 708 of substantially the same diameter as the O-ring 704. A cap 710 retains the sensing element 706 by compressing the same between the O-rings 704 and 704. The cap 710 may be affixed to the housing 700 in any suitable manner, such as the press fit and threaded types discussed previously. An orifice 712 is included in the cap 710, and the remaining cavity may be filled with the low viscosity rubber discussed previously. Alternatively the construction shown in FIG. 5b may be utilized. It will further be appreciated that a ridge, such as the ridge 106 in FIG. 2a may be substituted for one of the O-rings, and vice versa. For each of the alternatives shown in FIGS. 5a-5c, electrical contact may be made with the sensing elements as discussed in connection with FIGS. 2a-2c.

Having fully described one embodiment of the present invention and several alternatives thereto, many equivalents and alternatives will be apparent to those skilled in the art, and are intended to be included within the scope of the present invention.

What is claimed is:

1. A transducer for noninvasively monitoring a vascular waveform comprising
   a housing forming two independent cavities therein,
   a pair of support members, one disposed in each of said cavities,
   a pair of sensing elements, one resting on each of said first support members in said cavities,
   a pair of retaining members, one disposed on top of each said sensing element in said cavities,
   a pair of retaining caps, each cap having an orifice therethrough, said retaining caps being affixed to said housing to cause each of said sensing elements to be positioned between said support member and said retaining members,
   pressure-transmitting means within each of said orifices for causing pressure waves impinging thereupon to be transmitted to the associated sensing element, each sensing element being responsive only to pressure waves entering its associated orifice.

2. The transducer of claim 1 wherein said support members are formed integrally with said housing.

3. The transducer of claim 2 wherein said retaining members are O-rings.

4. The transducer of claim 1 wherein said pressure-transmitting means is rubber and fills substantially all of said cavity accessible through said orifice.

5. A transducer adapted for use in differential measurement comprising first and second pressure sensitive elements disposed parallel to one another, a plate member disposed between the first and second pressure sensitive elements for isolating the pressure sensitive elements from one another such that movement of one of the pressure sensitive elements does not cause movement in the other pressure sentitive element, first support means disposed between the first pressure sensitive element and the plate member, second support means disposed between the second pressure sensitive element and the plate member, the first and second support means configured to support at least the periphery of the respective pressure sensitive elements while permitting substantially free movement of the interior thereof, and retainer means associated with at least the first and second pressure sensitive elements for firmly maintaining the position of the first and second pressure sensitive elements with respect to the plate member and the first and second support means.

6. The transducer of claim 5 wherein the pressure sensitive elements are piezoelectric elements.

7. The transducer of claim 5 wherein the pressure sensitive elements are coated by a pressure-transmitting means.

8. The transducer of claim 5 wherein the first and second support means are O-rings.

9. The transducer of claim 6 wherein the plate member is affixed to the retainer means.

10. The transducer of claim 9 wherein the plate member is part of a housing, and the retainer means attaches to the housing.

11. A transducer adapter for use in differential measurement comprising a first piezoelectric disc, a second piezoelectric disc of substantially the same dimensions as the first piezoelectric disc and disposed substantially parallel thereto, a rigid circular plate of substantially the same diameter as the piezoelectric disc disposed between the first and second piezoelectric discs for isolating the first piezoelectric disc from the second piezoelectric disc, a pair of O-rings for supporting only the periphery of the piezoelectric elements, one O-ring disposed between the first piezoelectric disc and the circular plate and the other O-ring disposed between the second piezoelectric disc and the circular plate, retainer means for firmly positioning the first O-ring between the first piezoelectric disc and the circular plate and also firmly positioning the second O-ring between the second piezoelectric disc and the circular plate, and output means for providing output signals representative of the movement of the first piezoelectric disc and the second piezoelectric disc.

* * * * *